(12) United States Patent
Marsteller et al.

(10) Patent No.: US 7,554,658 B2
(45) Date of Patent: Jun. 30, 2009

(54) CUVETTE AND CUVETTE CAP

(75) Inventors: Laurence Marsteller, Tucson, AZ (US);
Harold K. Cauthen, Sonoita, AZ (US);
Wade Martin Poteet, Tucson, AZ (US);
Jose Carlos Alverez, Tucson, AZ (US);
Stuart Clark Poteet, Tucson, AZ (US)

(73) Assignee: CDEX, Inc., Tucson, AZ (US)

( * ) Notice: Subject to any disclaimer, the term of this patent is extended or adjusted under 35 U.S.C. 154(b) by 187 days.

(21) Appl. No.: 11/349,335

(22) Filed: Feb. 8, 2006

(65) Prior Publication Data

US 2007/0019189 A1    Jan. 25, 2007

Related U.S. Application Data

(60) Provisional application No. 60/650,525, filed on Feb. 8, 2005.

(51) Int. Cl.
*G01N 1/10* (2006.01)
(52) U.S. Cl. ...................................................... 356/246
(58) Field of Classification Search .................. None
See application file for complete search history.

(56) References Cited

U.S. PATENT DOCUMENTS

| | | | | |
|---|---|---|---|---|
| 4,648,713 | A | * | 3/1987 | Borer et al. ................. 356/246 |
| 5,651,940 | A | * | 7/1997 | Buonaiuto et al. ........... 422/102 |
| 6,249,345 | B1 | * | 6/2001 | Kraack et al. ............... 356/246 |

* cited by examiner

*Primary Examiner*—Michael P Stafira
(74) *Attorney, Agent, or Firm*—William F. Nixon; Law Office of William Nixon

(57) ABSTRACT

The invention provides a cuvette apparatus having two cavities that are in fluid communication with each other. The first cavity is larger than the second cavity an receives a fluid to be studied. The second cavity holds the fluid for analysis and is bounded by at least two thin walled windows that allow superior transmission of UV waves.

20 Claims, 9 Drawing Sheets back side view first side view

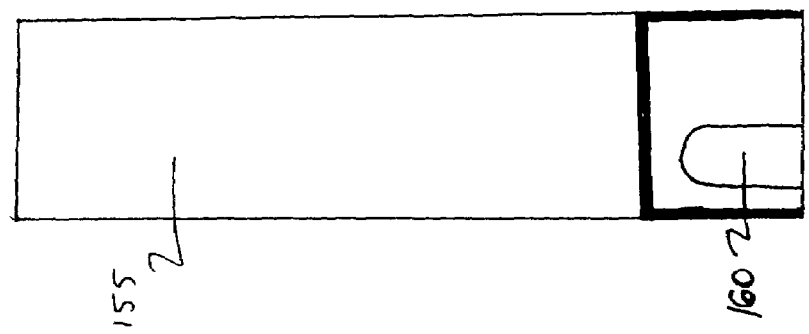
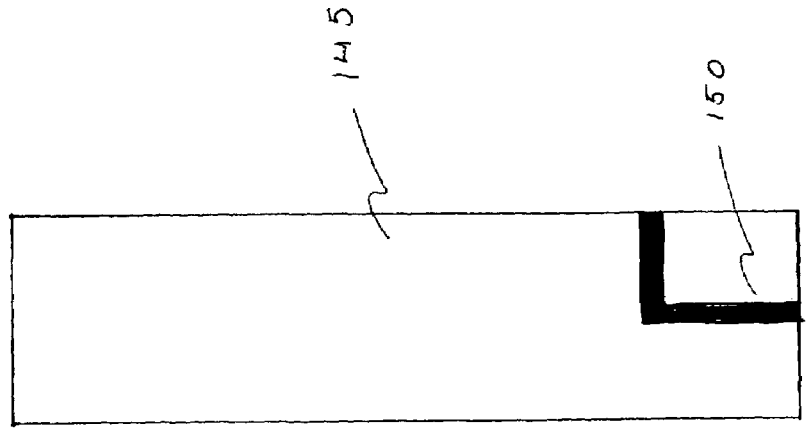

Bottom view

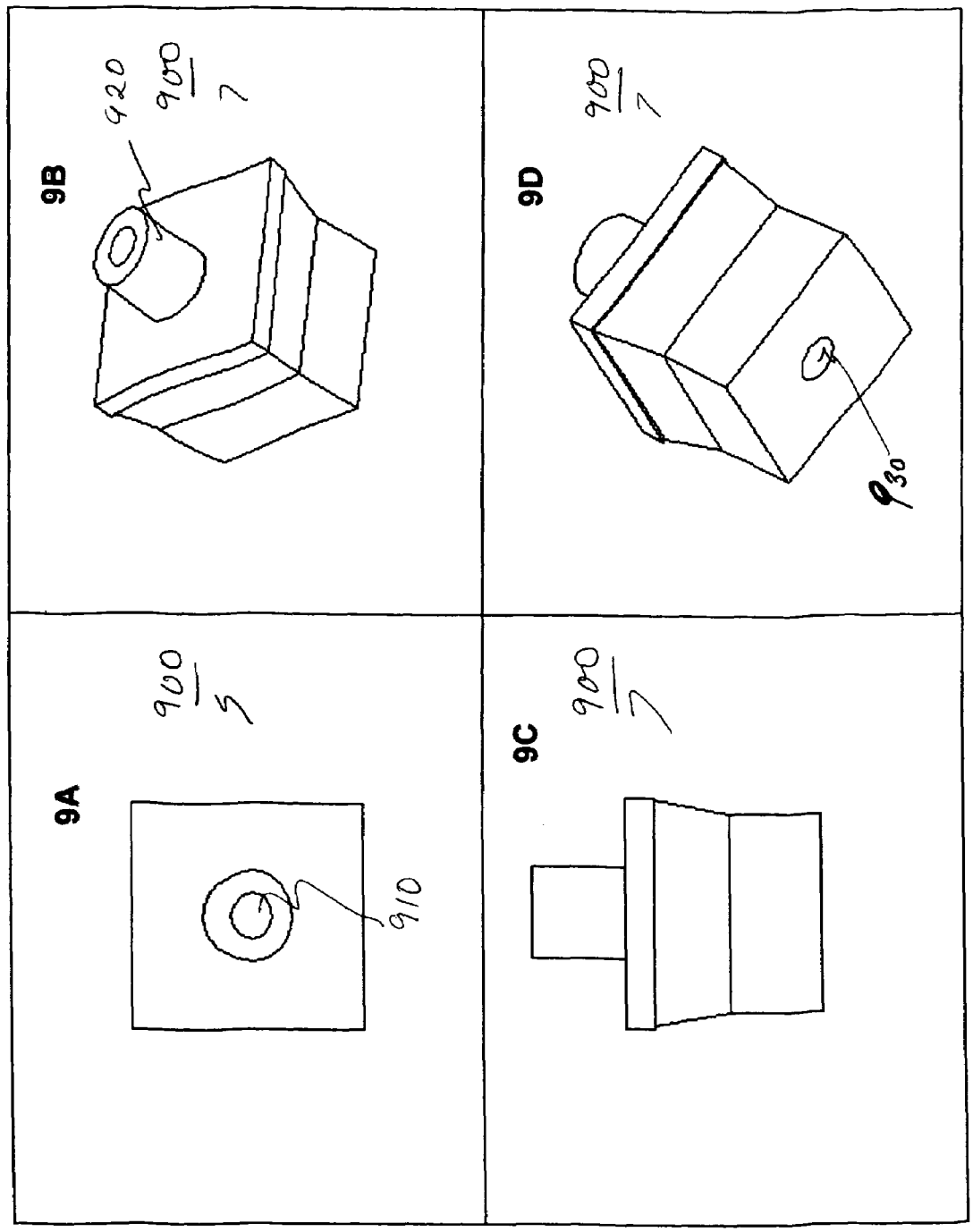

CUVETTE AND CUVETTE CAP

CROSS REFERENCE TO RELATED APPLICATION

This application claims priority under 35 U.S.C. 119(e) to U.S. Provisional Application No. 60/650,525 filed on Feb. 8, 2005, the disclosure of which is incorporated herein by reference.

BACKGROUND OF THE INVENTION

1. Field of the Invention

The invention relates to a cuvette for measuring the absorption or other optical characteristics of irradiation in liquid samples and to a cap apparatus for a cuvette or test tube that allows substances to be introduced into the cuvette, while providing a seal that prevents leakage of the substances and/or the escape of vapors from the cuvette.

2. Description of the Related Art

Cuvettes are typically used in laboratory, medical and/or chemical testing and manufacturing settings where they are used to store and also mix various substances. Cuvettes typically have a square shape, but may also be rounded. Cuvettes may be used for performing diagnostic tests on a sample, such as spectrophotometrical absorbance measurements or fluorescence polarization measurements. Conventional cuvettes typically require a large amount of the substance to be tested and are not made up of highly UV transmissive materials. In addition, many conventional cuvettes are not compatible with testing apparatuses.

In some cases, the substances being stored and/or mixed within the cuvettes may be toxic or otherwise hazardous. Thus, lab personnel or pharmacists who are mixing these types of substances may be exposed to hazardous materials. For example, pharmacy personnel may transfer chemotherapy drugs from an admixture compounding setup into a cuvette for subsequent testing. These drugs may vaporize or aerosolize when being injected into the cuvette, exposing the pharmacists to hazardous vapors. Thus, an apparatus that seals the cuvette so as to prevent the escape of vapors, while still allowing new substances to be injected into the cuvette is desirable.

SUMMARY OF THE INVENTION

The invention provides a cuvette for measuring the absorption or other optical characteristics of irradiation in liquid samples. The invention also provides for a cuvette cap that that allows the cuvette to be filled, while still providing a sufficient seal so that fumes and vapors do not escape from the cuvette.

In accordance with the invention, a cuvette is provided that has a thin-walled region or windows that allow for superior transmission of UV spectrographic transmissions. The thin-walled region in accordance with the invention is located along the corners of two adjacent edges at the base of the cuvette. The thin walled window region has an arch-like shape and has a thin wall thickness in contrast to the thickness of the remaining cuvette. For example, the thickness of the thin wall window region may be on the order of 0.25 mm or less. The positioning of the thin walled window region is such that it is in alignment with UV spectrographic emission devices. The arch-like shape of the thin walled window region allows the device to provide a thin walled region without compromising the structural integrity of the cuvette. The thin walled window region also forms an internal cavity within the cuvette so that only small amounts of the material to be detected are necessary.

Thus, the invention provides a substantially rectangular cuvette that has two cavities (also called recesses). The first cavity provides an opening for receiving the liquid to be analyzed. The second cavity is smaller than the first cavity and is bounded by at least two arch-shaped windows. The at least two windows are made of a UV transmissive material and have a thickness that is less than that of the other surfaces of the cuvette. This reduced thickness allows for better UV transmission. The smaller size of the second cavity means that less fluid is necessary for testing purposes. The smaller cavity also allows for positive indexing which assures the correct orientation of the cuvette when placed within a holder for testing. This is because the "send" and "receive" thin windows must align with the "send" and "receive" ports. The thinner shape of the windows also allows for less "play" when the cuvette is placed in the analysis system since the thin windows of the cuvette are pushed against the "send" and "receive" ports of the cuvette holder. The configuration of the cuvette in accordance with the invention also allows the cuvette to still have a square foot print allowing the cuvette to stand upright even though fluid is funneled into an area (cavity) of smaller volume. This is in contrast to a funnel shaped cuvette that cannot stand upright.

The invention includes a cuvette that has a first planar side wall, a second planar side wall disposed substantially parallel to and opposing the first planar wall, a front side wall, a back side wall disposed substantially parallel to and opposing the front side wall, wherein the first planer side wall, the second planar side wall, the front side wall and the back side wall form a substantially rectangular body having an inner space for receiving a sample liquid, and a planar floor perpendicular to and connected to each of the first and second planer side walls, the front side wall and the back side wall, the planar floor having a opening to a lower cavity, the lower cavity having at least two planar windows of a thickness less than a thickness of the first planer side wall, the second planar side wall, the front side wall and the back side wall.

The invention also provides a cuvette having a rectangular body having a first recess for receiving a sample liquid and a second rectangular recess smaller than the first recess and in fluid communication with the first recess, the second recess having at least two UV transmissive windows.

In accordance with one embodiment of the invention, a Luer Lock and cuvette cap is provided. In this embodiment, a user, such as a pharmacists or technician takes a cuvette, snaps the square cuvette cap into the cuvette opening, then places the Luer Lock valve device onto the top of the cap and fits the Luer Lock valve to the cap. This seals the cuvette. Substances can be introduced into the cuvette via the Luer Lock valve and cap. The valve can be either manually closed or may be self sealing. In one embodiment, the Luer Lock valve can receive a syringe which can be used to inject a substance into the cuvette. In this configuration, the cuvette is sealed preventing spillage of the substances as well as the escape of any vapors. The cap is configured so as to form a seal between itself and the cuvette. In this embodiment, the cuvette can be constructed from any polymer or plastic material capable of being shaped so that it can be adapted to the opening of a cuvette. In addition, this embodiment contemplates both square shaped cuvettes as well as rounded test tubes.

In accordance with another embodiment, the cap is a hardened rubber stopper. The cap in this embodiment has a thin bladder on the top surface that is capable of being pierced by a syringe needle. In this embodiment, a user fits the cap into the cuvette forming a tight seal between the cuvette and the cap, thus preventing leakage liquids and vapors from the cuvette. A syringe needle can be stuck through the cap seal and the contents of the syringe can be injected into the cuvette. In this embodiment, the cuvette can be constructed from any rubber or rubber-type material or polymer that can be shaped so that it can be adapted to the opening of a cuvette. In addition, this embodiment contemplates both square shaped cuvettes as well as rounded test tubes.

The invention provides a cuvette cap which prevents substances from leaking or spilling from a cuvette and also prevents vapors from escaping the cuvette. The invention has application in a variety of industries where harmful substances are collected for mixing and/or testing, including medical, biological and chemical research, testing and manufacture.

BRIEF DESCRIPTION OF THE DRAWINGS

A more complete understanding of the present invention and advantages thereof may be acquired by referring to the following description taken in conjunction with the accompanying drawings, in which like reference numbers indicate like features, and wherein:

FIG. 4 is a view of a second side portion of a cuvette in accordance with an embodiment of the invention;

FIG. 5 is a view of a front side portion of a cuvette in accordance with an embodiment of the invention;

FIG. 9 provides various views of the cuvette cap in accordance with an embodiment of the invention;

DETAILED DESCRIPTION OF THE PREFERRED EMBODIMENTS

Figure 1:
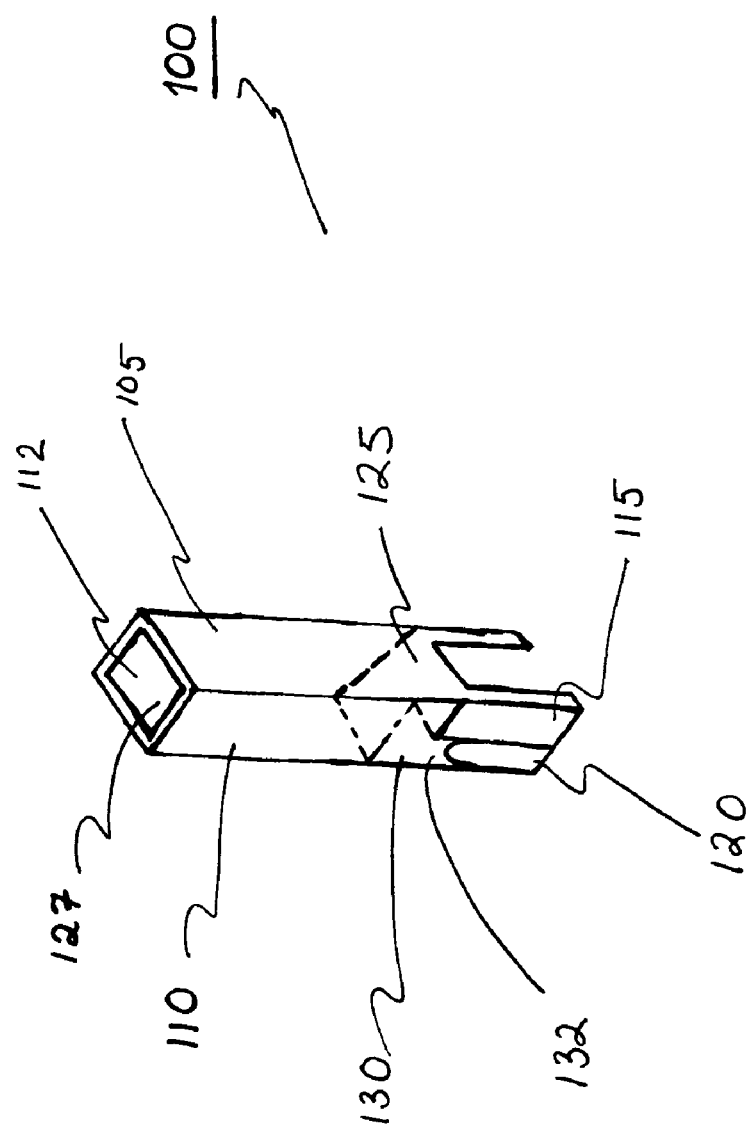
FIG. 1 is a perspective view of a cuvette in accordance with an embodiment of the invention.

FIG. 1 shows a perspective view of the cuvette 100 in accordance with an embodiment of the invention. FIG. 1 shows the front portion or wall 105 and the first side wall 110 of the cuvette. A back side wall and second side wall are not visible in FIG. 1 but are shown in the subsequent Figures. The side walls 110 and 145, the front wall 105 and the back side wall 135 of the cuvette form a well shaped opening 112 that allows liquids and other substances to be held in the cuvette. The base of the first side wall 110 is defined by two regions, 115 and 120. The region 115 has the same thickness as the rest of the cuvette structure. The second region 120, or arched window region is made of a material that is thinner than that of the rest of the cuvette. In one embodiment of the invention, the arched region is about 0.25 mm or less thick. As shown in FIG. 1, a base plane 125 is formed that is perpendicular to the side walls of the cuvette. The base plane 125 creates a first cavity (or recess) 127 that is bounded by the first and second side walls 110 and 135 and the front and back side walls 105 and 135. The base plane 125 has an opening 130 that opens to a second cavity (or recess) 132 within the cuvette. The cavity 132 is capable of holding a small amount of liquid. The cavity 132 is also bounded by the arched region 115 or window which thin wall relative to the thickness of the remaining cuvette structure. The cavity 132 is also bounded by at least one more thin walled arched region (window) (not shown) and may be bound on all four sides by such thin walled arched windows. The liquid to be examined occupies this second cavity 132.

It should be noted that the first cavity 127 is larger than the second cavity 132. The second cavity is bounded by at least two thin walled windows. The entire cuvette may be made of any UV transmissive material, such as Lexan. In order to provide structural integrity to the cuvette, the entire cuvette cannot be made of a thin walled material. Thus, only the arched region 115 (window), where the UV spectrographic device will be utilized, is thin walled. The arched structure of the windows also provides the cuvette with further structural integrity despite the thin walled region. The resulting cuvette has a thin walled detection region that allow for better UV transmission while still allowing the cuvette to have excellent structural integrity. The fact that the second cavity 132 is relatively small means that less sample volumes are required for testing.

Figure 2:
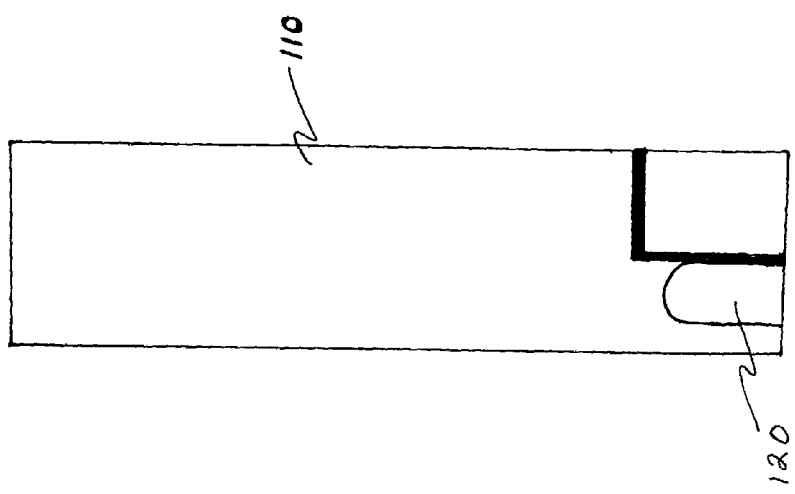
FIG. 2 is a view of the back side portion of a cuvette in accordance with an embodiment of the invention.

FIG. 2 shows a planar view of the back portion or wall 135 of the cuvette in accordance with the invention. FIG. 2 also shows a second arched (window) region 140 that is adjacent to the arched region 115 shown in FIG. 1. Together, the arched (window) region 115 and the second (window) arched region 140 form two of the four side walls of the cavity 132 for holding the liquid to be tested. The two other side walls that make up the cavity are internal to the cuvette but may also be thin walled arched windows.

Figure 3:
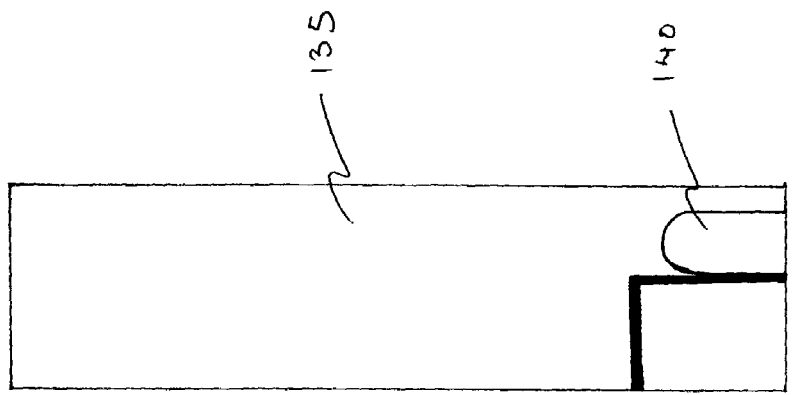
FIG. 3 is a view of a first side portion of a cuvette in accordance with an embodiment of the invention.
Figure 6:
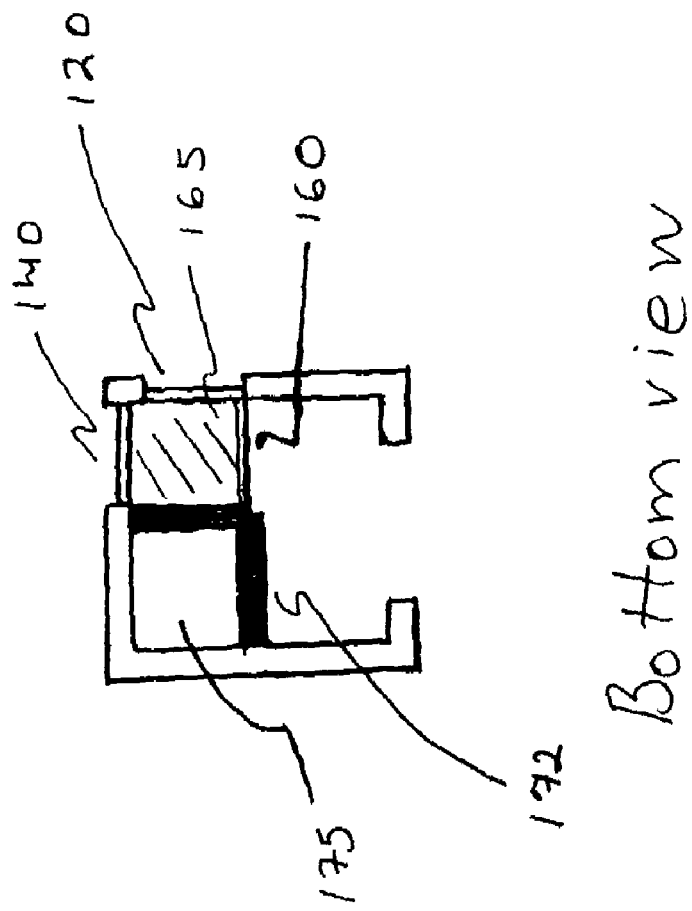
FIG. 6 is a view of the bottom portion of a cuvette in accordance with an embodiment of the invention.

FIG. 3 shows a planar view of the first side wall 110 also shown in FIG. 1. FIG. 3 also shows the arched (window) region 120 which is a thin walled region allowing superior UV wave transmissions. The arched region 120 is one of the side walls forming the cavity 132 also described in reference to FIG. 1 above. FIG. 4 shows a view of a second side wall 145 of the cuvette in accordance with the invention. The wall 145 is formed to reinforce the structure of the cuvette and has a thickness that is the same or about the same as the cuvette body. The second side wall 145 does not have a window. FIG. 5 illustrates a front view of the cuvette showing a front wall 155. As can be seen in FIG. 5, the front wall 155 has a section that is cut way near its base. The cut away exposes a third arched (window) region 160 that forms the third wall of the cavity 132 shown in FIG. 1. FIG. 6 illustrates a bottom view of the cuvette. The shaded region 165 is bottom view of the cavity 132. The cavity is bounded by the three thin walled windows 160, 140 and 120 and a fourth wall 175 that has a thickness that is the same as the rest of the cuvette body. A plane 172 also reinforces the cuvette providing additional structural integrity.

Figure 7:
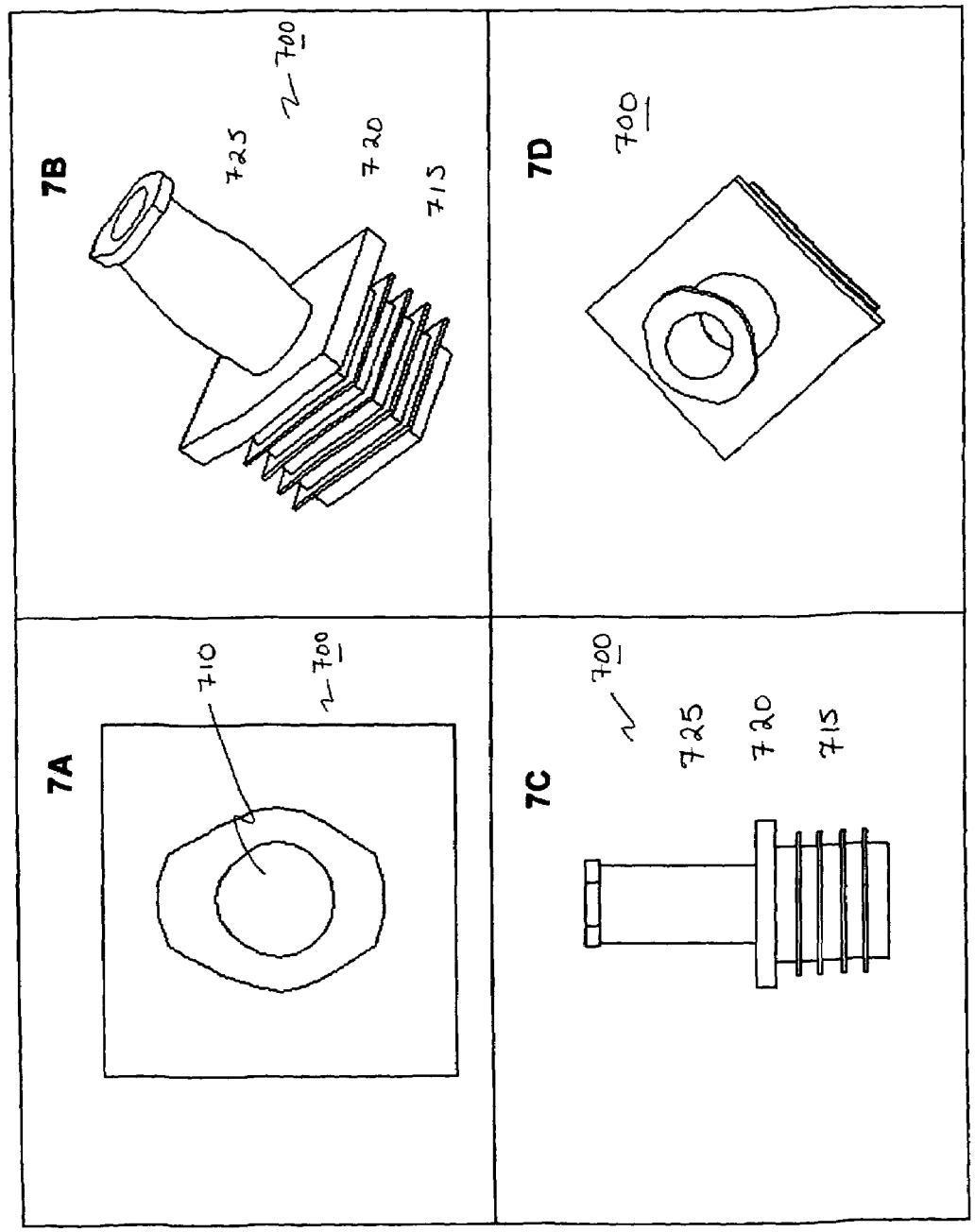
FIG. 7 provides various views of the cuvette cap in accordance with an embodiment of the invention.

FIGS. 7A-D shows various views of the cuvette cap 700 in accordance with embodiments of the invention. FIG. 7A shows a top view the cuvette cap 700 that includes an opening 710 that allows access to the cuvette and also allows coupling to a Luer Locking device. FIG. 7B shows a perspective view of the cuvette cap. The cap can be described as having three regions which are denoted in the FIG. 7, as regions 715, 720 and 725. Region 715 provides ridges which extend downward from the cap 700 surface so as to ensure that the cap provides a tight seal with the cuvette. These ridges as fitted into the cuvette so that their surfaces are in close contact with the inner walls of the cuvette. Region 720 in FIG. 7B is the base top surface of the cuvette cap which forms a seal with the cuvette. In other words, when the cuvette cap 700 is mounted onto a cuvette, Region 720 forms a flat surface covering the cuvette opening, thereby preventing the leakage of substances from the cuvette as well as vapors from escaping the cuvette. Region 725 in FIG. 7B shows an opening through which substances can be deposited in the cuvette. Region 725 can also be mated to a Luer Lock device which allows substances to be injected from a syringe into the cuvette without any of the substances leaking. FIG. 7C also another view of the three distinct regions 715, 720 and 725. Region 715 is a ridged region that extends into the cuvette to form a tight seal. Region 720 is the top surface of the cap which forms a seal with the cuvette opening. Region 725 provides a opening which allows access to the cuvette and also allows the cap to be coupled to a Luer Lock. FIG. 7D shows another perspective view of the cuvette cap. As described earlier, in this embodiment, the cap 700 may be constructed from a variety of materials including various plastics and polymers capable of being formed to the configuration as shown.

Figure 8:
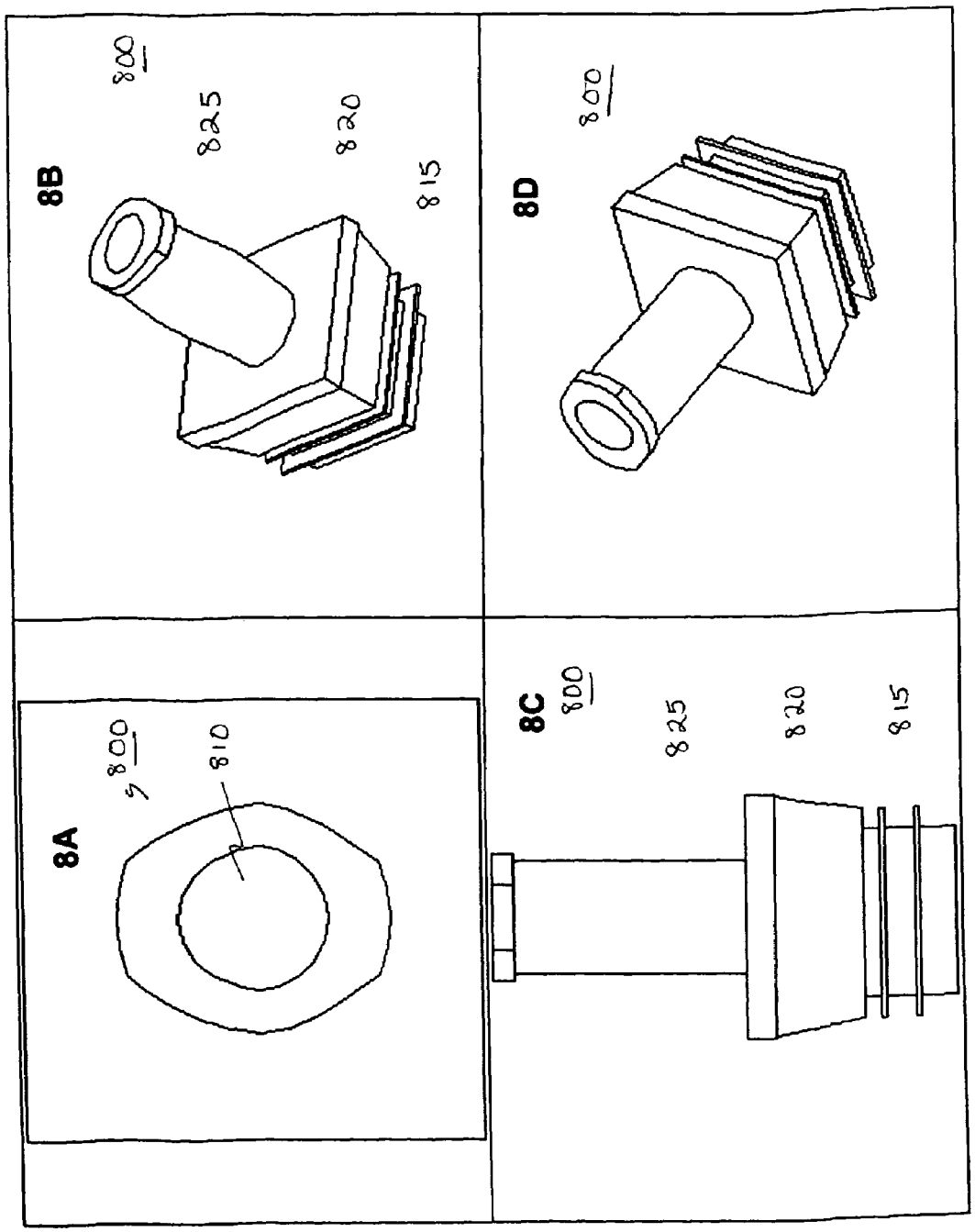
FIG. 8 provides various views of the cuvette cap in accordance with an embodiment of the invention.

FIGS. 8A-D shows various views of a cuvette cap in accordance with another embodiment of the invention. FIG. 8A shows a top view of the cuvette cap 800 which shows the flat top surface of the cap along with an opening 810 through which substances can be deposited into the cuvette. FIG. 8B shows a side view of the cuvette cap 800 in accordance with this embodiment. FIG. 8B can be described in conjunction with three separate regions denoted by the numerals 815, 820 and 825. Region 815 shows a ridged region which is inserted into the cuvette and which forms a tight seal between the cuvette and the cuvette cap 800. Region 820 is a top surface of the cap 800 which forms the seal between the cap 800 and the cuvette thus preventing leakage of substances as well as the escape of vapors from the cuvette. Region 825 acts as an adaptor which allows the cuvette cap 800 to be coupled to a Luer Lock and also allows those substances to be deposited into the cuvette. FIG. 8C is a side view of the cuvette cap which can also be described in conjunction with three regions 815, 820 and 825. Region 815 is a ridged portion which is inserted into and extends into the cuvette. Region 820 is the top surface of the cap 800 which forms a seal between cuvette and the cap 800. Region 825 allows the cuvette cap 800 to be coupled to a Luer Lock. Region 825 also allows substances to be flowed through into the cuvette. FIG. 8D also shows another side view of the cuvette cap 800.

FIGS. 9A-D shows the cap 900 in accordance with another embodiment of the invention. FIG. 9A is a top view showing both the top surface of the cuvette cap which forms a seal with the cuvette as well as an opening 910 which allows the cuvette to receive various substances. FIG. 9B shows a side view of the cuvette cap 900 in accordance with this embodiment. FIG. 9B shows the cuvette cap 900 in the form of a stopper which is inserted into the cuvette forming a tight seal which prevents leakage of various substances, including vapors from the cuvette. A rounded nub 920 is located on the top surface of the cap 900 which forms an opening through which substances can be deposited into the cuvette. For example, a syringe may be inserted into this opening and substances from the syringe can be injected into the cuvette with risk of leakage. FIG. 9C shows another side view of cuvette cap 900. FIG. 9D shows another perspective view of the cap 900 in accordance with this embodiment. FIG. 9D shows the bottom surface of the cuvette cap 900 which shows a bottom opening 930 through substances are flowed into the cuvette. As described above, in this embodiment, the cuvette cap 900 may be formed of a rubber or rubber like plastic or polymer.

Figure 10C:
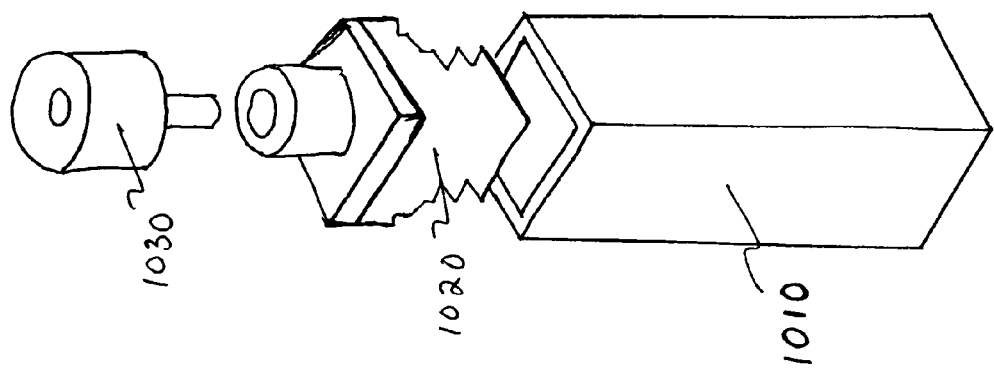
FIG. 10 provides perspective views of the cuvette cap mounted to a cuvette and fitted with a Luer Lock adapter and Luer Lock in accordance with one embodiment of the invention.
Figure 10B:
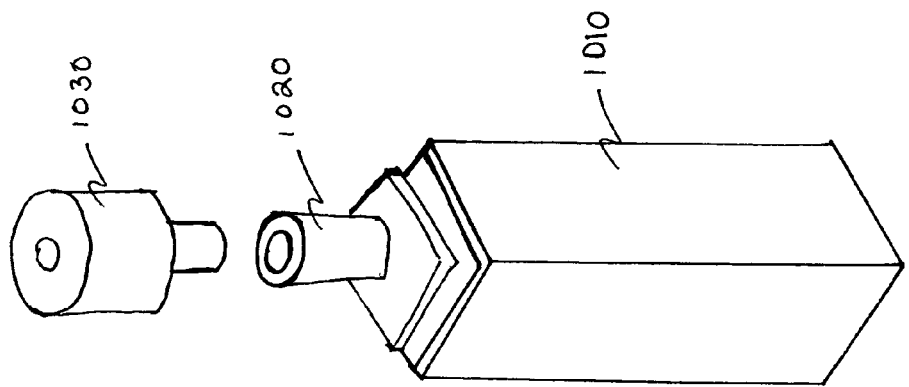
Figure 10A:
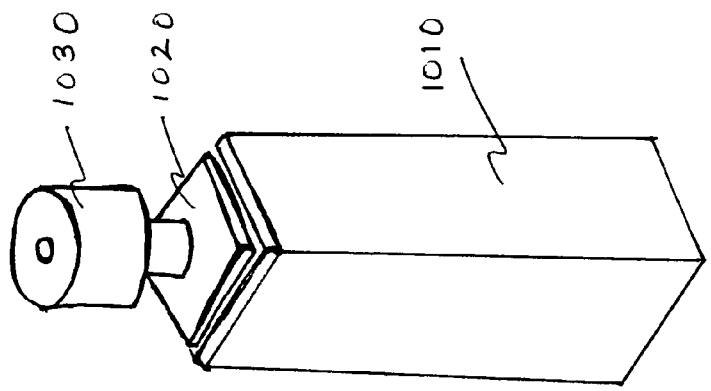
Figure 11D:
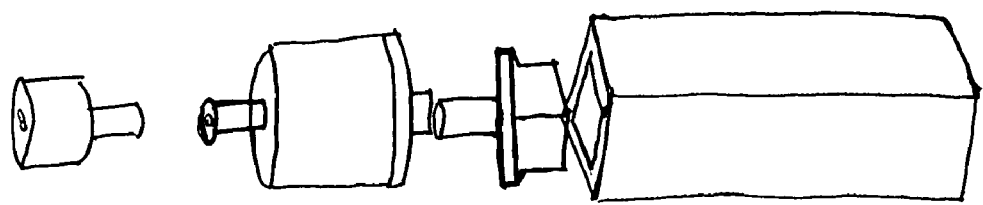
FIG. 11 provides perspective views of the cuvette cap mounted to a cuvette and fitted with a Luer Lock in accordance with one embodiment of the invention.
Figure 11C:
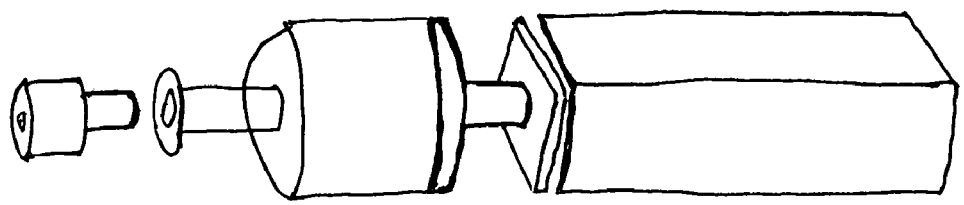
Figure 11B:
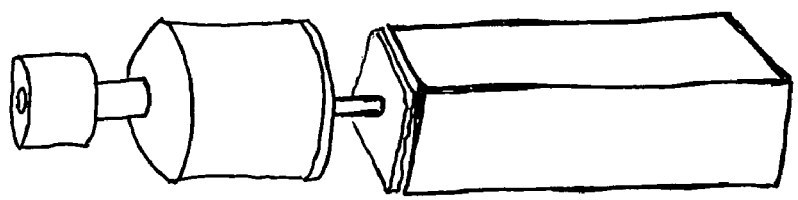
Figure 11A:
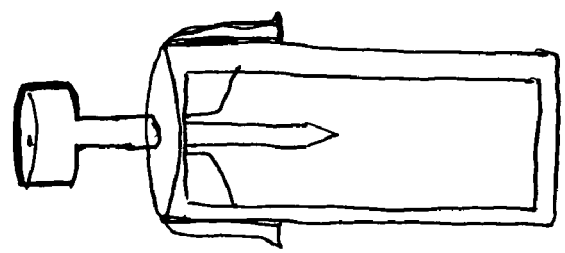

FIGS. 10A-C show the cap 1000 in accordance with an embodiment of the invention along with various components that are used in conjunction with the cap. FIG. 10A shows three components, a cuvette 1010 itself in which various substances are poured and/or mixed for study and analysis. A cuvette cap 1020 is shown in accordance with an embodiment of the invention, which has been inserted into cuvette to form a seal. A Luer Lock 1030 is shown which is fitted onto the top surface of the cuvette cap. FIG. 10B shows a second perspective view of this embodiment whereby the Luer Lock 1030 is not fitted onto the top surface of the cuvette cap 1020. FIG. 10C shows all three components, the cuvette 1010, the cuvette cap 1020 and the Luer Lock 1030 before they are coupled. Thus, a pharmacist or other technician places the cuvette cap 1020 firmly into the cuvette 1010 forming a seal between the cuvette 1010 and the cuvette cap 1020 which prevents leakage of substances. Luer Lock valve device 1030 is then fitted and sealed on to the cap. The Luer Lock 1030 is then capable of receiving an instrument, such as a syringe, which can inject substances into the cuvette via the lock and the cuvette cap.

FIG. 11 shows another embodiment of the cuvette cap. FIG. 11 shows an embodiment of the cuvette cap where the cuvette cap may be a rubber or rubber like plastic or polymer. FIG. 11A shows a cuvette cap inserted into the cuvette so as to form a seal therebetween. The cuvette cap is then mated to a Luer adaptor capable of receiving Luer Lock. Once the Luer Lock in FIG. 11A is fitted into the Luer adaptor, a syringe can then be inserted via the Luer Lock and can puncture the cuvette cap allowing the contents of the syringe to be deposited into the cuvette. FIG. 11B shows the components of FIG. 11A before those components are fully assembled. In FIG. 11B, the cuvette, cuvette cover, Luer adaptor and Luer Lock can all be seen. In FIG. 11C also shows another view of each of the components described above before they are entirely assembled. In FIG. 11C, the cuvette cap is still inserted into the cuvette. In this figure, the Luer adaptor and the Luer Lock have not yet been assembled. FIG. 11D shows all of the components described above prior to assembly. Thus, FIG. 11D shows the cuvette, the cuvette cap which has not yet been inserted into the cuvette, the Luer adaptor which has not yet been connected with the cuvette cover and the Luer Lock which has not yet been connected with the Luer adaptor. Once these components are assembled, as shown in FIG. 11A, any pharmacist or other technician can insert a syringe into the cuvette via the Luer Lock, a Luer Lock adaptor and cap. In this manner, substances can be injected into the cuvette without any of the substance escaping.

We claim:

1. A cuvette, comprising: a first planar side wall; a second planar side wall disposed substantially parallel to and opposing the first planar wall; a front side wall; a back side wall disposed substantially parallel to and opposing the front side wall, wherein the first planer side wall, the second planar side wall, the front side wall and the back side wall form a substantially rectangular body having an inner space for receiving a sample liquid; a planar floor perpendicular to and connected to each of the first and second planer side walls, the front side wall and the back side wall, the planar floor having a opening to a lower cavity, the lower cavity having at least two planar windows of a thickness less than a thickness of the first planer side wall, the second planar side wall, the front side wall and the back side wall.

2. The cuvette according to claim 1, wherein the at least two planer windows have an arched shaped.

3. The cuvette according to claim 1, wherein the at least two planar windows are made of a UV transmissive material.

4. The cuvette according to claim 1, wherein the at least two planar windows have a thickness of about 0.25 mm or less.

5. The cuvette according to claim 1, wherein the cuvette is made by one of molding and machining.

6. A cuvette comprising:
a rectangular body having a first recess for receiving a sample liquid; a planar floor located perpendicular to said first recess;
a second rectangular recess smaller than the first recess and in fluid communication with the first recess, wherein the second recess is located near the external corner of two intersecting perpendicular faces of the rectangular body and having at least two UV transmissive windows adapted to shorten the optical path length between the windows.

7. The cuvette according to claim 6, wherein the at least two planar windows have an arched shape.

8. The cuvette according to claim 6, having a thickness of about 0.25 mm or less.

9. A substantially rectangular cuvette, comprising: a first end portion; a second end portion; a planar floor formed between the first end portion and the second end portion; the first recess formed between then first end portion and the planar floor; a second recess formed between the second end portion and the planar floor, wherein the first recess has a larger volume than the second recess, and the second recess has at least two windows, the two windows having a thickness less than that of other regions of the cuvette.

10. The cuvette according to claim 9, wherein the planar floor has an opening allowing the first recess and second recess to be in fluid communication.

11. The cuvette according to claim 9, wherein the at least two window are UV transmissive and have an arched shape.

12. The cuvette according to claim 9, wherein the at least two windows have a thickness of 0.25 mm or less.

13. A substantially rectangular cuvette, comprising:
a first cavity formed by four sidewalls of substantially equal thickness;
a second cavity having at least two windows, the two windows having a thickness less than the thickness of the four side walls of the first cavity, the first and second cavities being in fluid communication with each other, wherein a third window of the second cavity is coaligned with one other window and on the opposing wall perpendicular from the other window.

14. The cuvette according to claim 13, wherein the at least two side walls have an arched shape.

15. The cuvette according to claim 13, wherein the at least two windows have a thickness of about 0.25 mm or less.

16. The cuvette according to claim 13, wherein the third window has attached, applied, or in close proximity, a reflective surface to increase the light exiting the opposite window.

17. A substantially rectangular cuvette, comprising:
a first cavity formed by four sidewalls of substantially equal thickness; a planar floor located perpendicular to said first cavity
a second cavity having at least two windows, the two windows having a thickness less than the thickness of the four sidewalls of the first cavity, the first and second cavities being in fluid communication with each other, wherein the bottom of the cuvette has a rectangular opening to allow an optical measuring system to be positioned near the windows in the second cavity, wherein the windows have an optical path length less than the shortest sidewall of the first cavity and wherein the rectangular opening allows a precise fit into a corresponding protrusion in an external mounting device thus providing the capability of repeatable positioning of the cuvette within the optical measuring system.

18. The cuvette according to claim 17, wherein the at least two windows have an arched shape.

19. The cuvette according to claim 17, wherein the at least two windows have a thickness of about 0.25 mm or less.

20. The cuvette according to claim 17, wherein a third window has attached, applied, or in close proximity, a reflective surface to increase the light exiting the opposite window.

* * * * *